(12) United States Patent
Feeser et al.

(10) Patent No.: US 6,245,098 B1
(45) Date of Patent: Jun. 12, 2001

(54) CATHETER SYSTEM WITH HIGH KINK RESISTANCE

(75) Inventors: Jörg Feeser; Wolfgang Supper, both of Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/448,537

(22) Filed: Nov. 22, 1999

Related U.S. Application Data (63) Continuation of application No. PCT/EP98/03072, filed on May 25, 1998.

(30) Foreign Application Priority Data

May 23, 1997 (DE) ............................................... 197 21 703

(51) Int. Cl.[7] ............................... A61M 29/00; A61F 2/06
(52) U.S. Cl. .................................................................. 623/1.1
(58) Field of Search .................................... 606/198, 194, 606/190, 108; 623/1.11, 1.12; 604/103, 103.1

(56) References Cited

U.S. PATENT DOCUMENTS

| | | |
|---|---|---|
| 4,636,346 | 1/1987 | Gold et al. . |
| 5,334,171 | 8/1994 | Kaldany . |
| 5,524,337 | 6/1996 | Houser et al. . |
| 5,569,221 | 10/1996 | Houser et al. . |

FOREIGN PATENT DOCUMENTS

| | | |
|---|---|---|
| 2187592 | 5/1997 | (CA) . |
| 0 303 487 | 2/1989 | (EP) . |
| 0 742 030 | 11/1996 | (EP) . |

*Primary Examiner*—Henry J. Recla
*Assistant Examiner*—Vy Q. Bui
(74) *Attorney, Agent, or Firm*—Morrison & Foerster LLP; Todd W. Wight (57) ABSTRACT

A catheter system (1) which is useable as a part of a delivery kit for introducing objects (8) into the living body is provided which has a very high flexibility with simultaneous kink resistance and via which compressive as well as tensile forces are reliably transmittable. It comprises at least one longitudinally extended inner catheter (4) and at least one accessory component (6, 10) which is arranged in the distal end region of the inner catheter (4), wherein the end-face is abutted on at least a portion of the accessory component (10) such that movement of the accessory component (10) relative to the longitudinal extent of the inner catheter (4) is prevented.

23 Claims, 5 Drawing Sheets

CATHETER SYSTEM WITH HIGH KINK RESISTANCE

This is a continuation of International Application No. PCT/EP98/03072, with an international filing date of May 25, 1998.

TECHNICAL FIELD

The present invention relates to a catheter system which is useful as a delivery kit for introducing objects into the living body.

BACKGROUND

Catheter systems of this type are often used to introduce endoprostheses into the human body in order to place and implant these there. In this sense, endoprostheses are typically stents, traps (filters) or coils (spools). The kits used to introduce these objects generally consist of a catheter (shaft) assembly and a handle part, whereby the handle part is constructed on the one hand to exercise the compressive force which necessarily occurs with the introduction of the kit tip into the body through the circulation system or other very narrow body vessels and, on the other hand, to promote depositing or placement accuracy. In this connection, endoprostheses are firmly anchored on the catheter and are simultaneously introduced into the body therewith. In order to reach the placement site in a targeted manner, these guide catheters must be highly flexible and able to withstand compression at the same time. In order to be able to exactly determine at which place in the body the endoprostheses are deposited, radiopaque markers are in general fixed in the distal end region of the catheter, neighboring the endoprostheses. With trans-illumination of the body, for example by means of x-ray irradiation, these markers remain visible such that the endoprostheses can also be located relative to the body, provided that they do not change their position relative to the markers and the markers do not change their position relative to the catheter.

Therefore, catheter systems as a part of a delivery kit have been proposed in which the markers are ring-like accessory components which are adhered to an inner catheter. Cyanoacrylate compounds are frequently used as an adhesive. They have the advantage that they cure particularly quickly and are suitable for narrow adhesion gaps. In general, however, adhesive compounds have the disadvantage that the cured adhesive negatively influences the mobility or flexibility of the catheter at the region of adhesion. The cured adhesives which are often glass-hard are in their flexibility greatly in contrast to the flexible catheter materials. Thus, stress peaks and fractures of the catheter material can arise at the adhered regions. As a consequence, curing disadvantageously influences the mobility of the kit tip. When the delivery kit is then introduced into the body under increased application of force and the catheter tip is necessarily forced around a diversion or bend, the flexibility required for this exceeds the actual flexibility which is limited by the adhesives. Mechanical failure of the catheter results. This mechanical failure mostly occurs in the form of kinks such that further introduction of the catheter is made impossible. Furthermore, removal by suction through the lumen formed by the inner catheter is made impossible by the kink. It is also possible that mechanical failure occurs in the form of fractures so that not only the further introduction of the catheter is no longer possible, but also sharp-edged fractures possibly injure the body vessels and detached fragments can be washed away by e.g. blood and remain in the human organism.

SUMMARY OF THE INVENTION

Therefore, the object of the present invention is to provide a catheter system that has very high flexibility with simultaneous kink resistance, via which compressive and tensile forces are reliably transferable, and on which accessory components, such as irradiation impermeable and radiopaque markers or endoprostheses, do not change their position relative to the catheter tip and relative to each other during the introduction process. Furthermore, an object of the present invention is to provide a catheter system with which, even in case of mechanical failure in the form of fracture, fragments are reliably removable from the body without injuring the human body upon fracture or upon removal of the broken catheter.

These objects are advantageously solved by a catheter system with at least one longitudinally extending inner catheter and at least one accessory component which is arranged in the distal end region of the inner catheter around the inner catheter, wherein the catheter system further comprises a tightly fitted tubular element on the inner catheter with at least one end-face, wherein the end-face abuts on at least one section of the accessory component in such a manner that movement of the accessory component relative to the longitudinal extent of the inner catheter is prevented. The tubular element is in tension around the inner catheter. Components such as radiopaque markers, stents, filters, coils, endoscopic tools or the like are to be understood as accessory components within the meaning of this solution of the underlying problem according to the invention. The distal end region of the inner catheter denotes the region of the inner catheter which is facing the body interior. By tightly affixing a tubular element on the inner catheter, movement of the accessory components on the inner catheter is prevented by abutting the accessory component or the accessory components to the end-face or end-faces of the tubular element. Furthermore, a total peripheral spanning of the inner catheter is obtained whereby additionally tensions occurring with deviations of the catheter can be partially taken up by the tubular element and as a consequence the inner catheter is relieved. The form locking effect by abutment on the end-face prevents relative movement between accessory component and tubular element. Since the tubular element is additionally tightly fitted on the inner catheter, the relative movement between the accessory component, or, optionally accessory components, and the inner catheter is also advantageously excluded. Correspondingly, the distal end region of the inner catheter is flawlessly identifiable and the location of the object to be introduced is clearly determined in an advantageous manner with customary diagnosis methods, such as ultrasound or x-ray irradiation for example. Through the abutment of the end-face on at least a portion of the accessory component or accessory components, it is ensured that this end-face of the accessory component or components can simultaneously serve as an abutment surface for further components. Additionally, by providing a tubular element, it is also insured that the fragments arising by fracture of the catheter system are held back and are then hampered from spreading into the organism.

The invention is based on the concept of providing a delivery kit with a catheter system in which the accessory components that are necessarily found on the catheter cannot move in their position relative to the center-line of the catheter, but at the same time, upon deformation of the inner catheter, microscopic relative movements between these components and the inner catheter are enabled. Thus, possible kinks are prevented.

According to an advantageous embodiment, the end-face and/or end-faces is (are) substantially formed at a right-angle to the longitudinal extent of the inner catheter. This advantageous further embodiment of the inventive catheter system ensures definitive abutment surfaces which are particularly simple to form and furthermore additionally ensures that an installation direction does not have to be taken into account when mounting the catheter system. Mounting is simplified therewith.

According to another preferred embodiment of the present invention, affixing of the tubular element to the inner catheter occurs by melting. Melting of the tubular element insures an attachment between the element and the inner catheter which is equal to a adhesive bond in its attachment force, whereby neither hardening of the adhesive nor an enbrittlement of the material to be adhered occurs.

Affixing the tubular element by shrinking to the inner catheter is also provided. This fastening mechanism insures similar adhesion conditions, but simplifies the control of the process parameters when mounting catheter system according to the invention.

In order to affix the tubular element better to the inner catheter and to simultaneously mount the catheter in the regions neighboring the tubular element, and thus provide a mechanical load release, the catheter system is provided according to the invention such that it additionally comprises at least one tubular casing which is coaxially arranged around the inner catheter and the tubular element and is affixed to this.

To prevent the mostly rigid accessory components from negatively influencing the mechanical properties of the inner catheter, the catheter system is further advantageously provided according to the invention such that it additionally comprises a tubular cushion between at least one accessory component and the inner catheter.

It is also possible that the tubular casing runs between the accessory component and the inner catheter as a cushion. Equally as with the separately provided cushion, this cushion function prevents the edge regions of the accessory components from pressing directly into the inner catheter when the application kit is deviated or guided around bends and further prevents stress peaks at these spots which could possibly lead to an increased risk of mechanical failure.

In order to create a total peripheral initial tension around the inner catheter in the entire region of the catheter, and thus increase the mechanical load bearing capacity with respect to kinking of the catheter system, the tubular casing is advantageously arranged on substantially the entire longitudinal extent of the inner catheter around it and affixed to it. In this case, inner catheters can also be used which otherwise could not be used exposed or "naked" because of e.g. unfavorable material properties.

In a further advantageous embodiment of the catheter system according to the invention, the tubular casing is affixed by melting. It is also provided that the tubular casing can be affixed to the inner catheter by shrinking. A combination of these two fastening mechanisms is also possible. The advantageous fastening mechanisms according to the invention reduce the distance between tubular casing and accessory components and/or tubular casing and inner catheter which leads to an increased kink resistance and a larger maximal pressure load.

In order to span or compress the endoprosthesis to be introduced into the body, which typically consists of a resilient material such as plastic or metal, to its minimal diameter and to give it a defined position relative to the catheter, the catheter system according to the invention further comprises an outer sheath which is arranged coaxially around the tubular casing and the endoprosthesis when using the catheter system.

Radiopaque markers are advantageously provided as accessory components such that the catheter tip can be clearly localized by customary diagnosis devices.

Additionally, the catheter system according to the invention is additionally provided such that it encompasses a flexible tip which is glued to the distal end of the inner catheter. A particularly advantageous embodiment provides that the adhesive is cured by ultra-violet radiation, in which case the catheter tip is made from a UV-transparent material. The catheter tip is flexible and advantageously has a form which brings about a lower risk of injury and is suitable to induce the change of shape of the catheter.

According to an advantageous further construction, it is also within the scope of the present invention that the tip is melted to the distal end of the catheter. A melted connection insures similar mechanical properties as with an adhesive bond without leading to an embrittlement effect and without leading to a layer of cured adhesive in the flexible catheter tip region.

The inner catheter in the direction of extension of the catheter system is also provided such that it has sections of different diameter whereby at least some of the accessory components are at least partially capable of being abutted to the end-faces defined by the diameter alterations. At least some of the assembly operations can be omitted by this advantageous further construction because, as a result of the design of the inner catheter, end-faces are provided on which the accessory components and/or the object to be introduced into the body are abuttable in such a manner that they take up an axially fixed position in use of the catheter, which is necessary for determining the location or the catheter tip.

Advantageously it is also provided here that the end-faces of the diameter alterations are substantially formed at a right-angle to the direction of extension. This insures a clear fixation of position with simultaneous easier production of the diameter alterations and/or steps.

Polyamide or comparable materials which are capable of being melted at low temperature and are producible in a thin-walled manner represent a particularly preferred selection of materials for the tubular casing and/or the tubular element as a part of the catheter system according to the invention, as long as the tubular casing and/or the tubular element are affixed by melting to the inner catheter. By such a materials selection, it is possible to produce a particularly tight joint between tubular casing and/or tubular element and inner catheter whereby both components constitute protection of the inner catheter against mechanical damage.

Should the tubular casing and/or the tubular element be fixed to the inner catheter by shrinking, then polyester or a comparable thin-walled shrinking sheath material represents a particularly preferred materials selection because these materials have similar advantageous properties in a shrink process as those mentioned above in combination with the melt process.

It is equally conceivable to affix the tubular casing by shrinking and the tubular element by melting to the inner catheter or to provide a correspondingly reciprocal mixed arrangement. This arrangement offers the advantage of dividing the inner catheter into different axial segments depending on the desired configuration.

Advantageously, the inner catheter is produced from one of the following materials:

polyimide, polyamide or comparable plastics of high strength. As a result of the design of the catheter system according to the invention, namely the protection of the inner catheter provided by the tubular casing and/or the tubular element, it is possible to select materials for the inner catheter which have excellent flexibility but which were avoided in conventional catheter construction based on other disadvantageous mechanical properties such as lower ductility or notch impact strength.

The catheter system according to the invention also permits particularly suitable dimensions to be provided for the introduction in narrow vessels of a living body such that, according to advantageous embodiment, the tubular element has a wall thickness of approximately 0.03 mm to 0.1 mm. The tubular casing is also advantageously further constructed in such a manner that it has a wall thickness of approximately 0.03 mm to 0.1 mm.

A particularly desirable construction of the inner catheter provides that it has a wall thickness of approximately 0.15 mm with a diameter of approximately 1.2 mm. This diameter to wall thickness ratio permits a thin design of the inner catheter with high kink resistance and high flexibility. The outer sheath provided according to an advantageous further construction has a wall thickness of approximately 0.15 mm with an inner diameter of approximately 1.8 mm according to a desirable construction. As a consequence, the catheter system according to the invention would have a total outer diameter from its handle portion to the distal end which is small in comparison to conventional delivery kits and whose resistance exceeds that of conventional systems.

Whether or not the above described catheter system according to the invention is an advantageous part of a delivery kit for endoprostheses, it is clear to the person skilled in the art that further uses are possible.

BRIEF DESCRIPTION OF THE DRAWINGS

In the following, examples are more closely described and explained with reference to the appended Figures for further illustration and better understanding of the invention.

DESCRIPTION OF THE PREFERRED EMBODIMENTS

Figure 1:
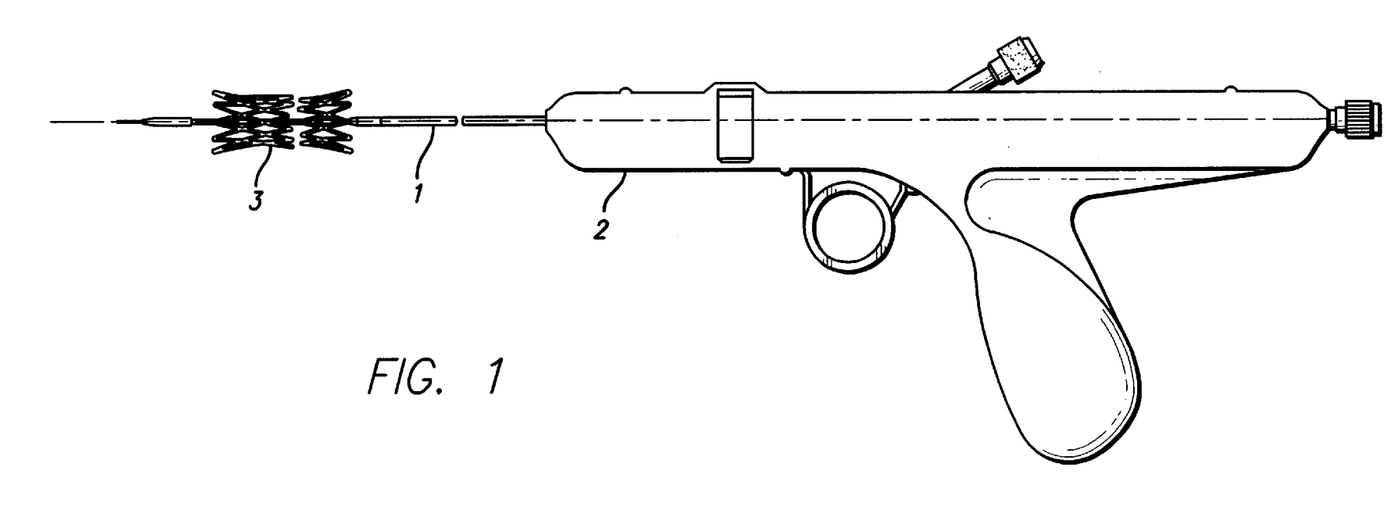
FIG. 1 shows a side view of the catheter system according to the invention as a part of a delivery kit whereby also the exemplary depicted handle and the exemplary endoprosthesis illustrated as a stent are depicted, which also belong to the delivery kit.

FIG. 1 provides an overview for a preferred delivery kit, depicted here as a system for introduction of an endoprosthesis 3 into a human body. Aside from the endoprosthesis 3, the delivery kit has a catheter system or shaft assembly 1 and a known handle 2. The endoprosthesis 3 preferably consists of resilient material such as metal or plastic. It is shown in the expanded state, i.e. depicted in the state in which it is in the body after the delivery kit is removed and the endoprosthesis 3 remains. The depiction in FIG. 1 expresses the diameter relationship between the catheter system 1 and the expanded endoprosthesis 3. However, it is to be noted that the catheter system 1 is depicted in a shortened form.

Figure 2:
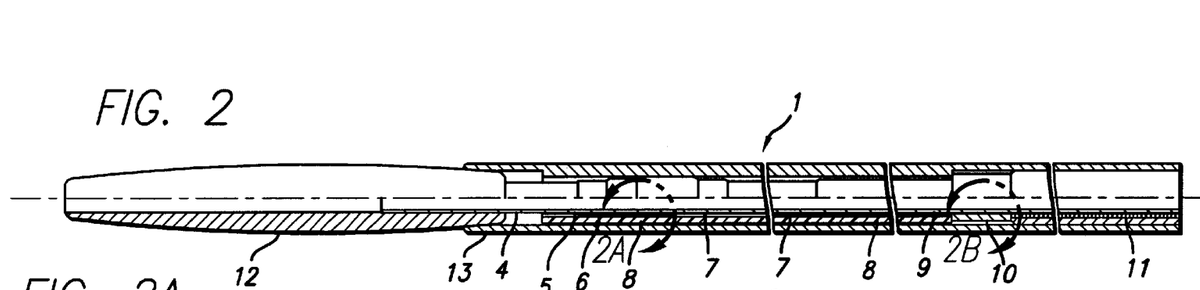
FIG. 2 shows a partially sectional side view of the distal end of the catheter system according to the invention in a first embodiment.
Figure 2A:
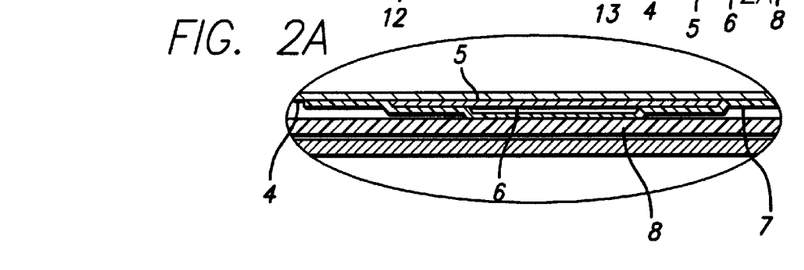
Figure 2B:
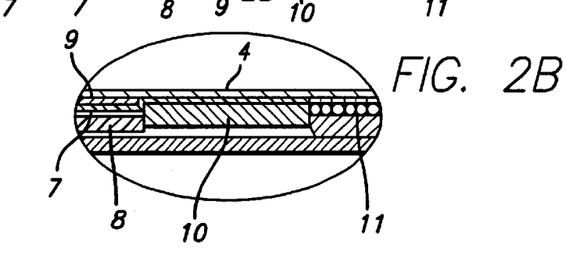

FIG. 2 shows in detail how the distal end region of the catheter system 1 is constructed. From the proximal end to the distal end of the catheter system 1, the following components are labeled in the Figure: filler 11, proximal radiopaque marker 10, tubular element 9, mounted endoprosthesis 8, tubular casing 7, distal radiopaque marker 6, cushion 5, inner catheter 4, outer sheath 13 and flexible tip 12.

In the lower half of FIG. 2, the individual structural elements of the catheter system are depicted in section whereas in the upper half of the Figure, the mounted endoprosthesis and/or the outer sheath 13 are depicted in a sectional side view and the other components are presented in a non-sectional side view.

In the following, the individual structural elements of the catheter system 1 are described in more detail.

The inner catheter 4 forms the innermost component and is formed here as a continuous inner catheter, i.e. is depicted as a component without alterations in diameter or steps. Preferably, it consists of high-strength polyimide as this material supports high kink resistance of the catheter system well. However, it is self-evidently possible to replace polyimide by other materials, for example, by polyamide. Mechanically strengthened "braided" plastics can also be used.

In the depicted preferred embodiment, a cushion 5 and a tubular element 9 are placed on the inner catheter 4. The cushion 5 is found under the distal radiopaque marker 6 and is provided there so that the marker 6 gently contacts the inner catheter 4. Markers 6, 10 typically consist of a platinum-iridium alloy or another x-ray impermeable material which produces good contrast and are adapted to be able to slide under friction on the inner catheter 4 so long as they are not separately fastened. With strong bending movement of the distal end region of the catheter system 1, cushion 5 prevents marker 6 from entrenching with its edges on inner catheter 4 and producing tension peaks there which eventually could lead to mechanical failure of the inner catheter 4 in this region. The tubular element 9 is arranged immediately distally from the proximal radiopaque marker 10. The tubular element 9 forms a cylinder which lies coaxial to the inner catheter 4 and has two end-faces. One of these end-faces is used as a mechanical stop or as an abutment surface for the proximal radiopaque marker 10.

The tubular element 9, the cushion 5 and the distal radiopaque marker 6 are totally peripherally encased by the tubular casing 7. This sheath serves to affix the previously mentioned components to the inner catheter 4. In the example presented here, the tubular casing 7 additionally extends to under the proximal radiopaque marker 10. Thus, a cushioning function is provided for the distal as well as for the proximal radiopaque marker such that the production of tension peaks during a change in shape of the catheter system 1 is counter-acted.

By affixing the cushion 5, the distal radiopaque marker 6 and the tubular element 9, abutment edges respectively result which prevent the possible movement of the components which are supported on the abutment edges in the axial direction relative to the inner catheter 4. As clearly emerges from FIG. 2, the proximal radiopaque marker 10 is supported on the proximal end-face of the tubular element 9. The end-faces of the radiopaque marker 10 and the tubular element 9 only partially overlap such that the endoprosthesis 8 in the mounted state can support itself in the same manner on the distal end-face of the proximal radiopaque marker 10. The proximal marker 10 is supported on its proximal side by a filler 11, a spring element in the example presented in FIG. 2, which can be produced from metal, plastic or comparable materials. The spring extends from the proximal radiopaque marker 10 up to the handle 2 depicted in FIG. 1.

As a consequence, it is possible to apply a compressive force via the handle 2 depicted in FIG. 1 onto the catheter system 1 and the accessory components found therein which is necessitated by introduction of the catheter system in a human body and/or pulling the sheath proximally for releasing the endoprosthesis. Hence, the arising compressive force flows from the handle 2 via the filler 11, in this case, a spring. The spring locks the proximal radiopaque marker 10 by form which in turn locks the tubular element 9 as well as the endoprosthesis 8 by form such that these components can consequently pass on the force and/or carry through the form-locking effect. As described above, the tubular element 9 is affixed to the inner catheter by the tubular casing 7. Additionally, the tip 12 which preferably consists of a soft elastomer attached to the inner catheter 4 offers a stop on the distal side for an endoprosthesis 8.

In this manner, each of the structural elements is hampered by the adjacent structural element from moving in the axial direction relative to the inner catheter 4 or to other components if a compressive force is applied to the catheter system 1, or from being isolated from the catheter system in case mechanical failure occurs. As will be evident to the skilled reader, the tubular element 9 enhances the mechanical properties of the inner catheter 4, such as the tensile strength and provides previously unknown emergency running properties and redundancy should mechanical failure occur.

In the example depicted in FIG. 2, the tip 12 is fastened to the inner catheter 4 by a suitable thermal joining method, e.g. heat sealing. It is also possible to form inner catheter 4 and tip 12 integrally.

The fastening mechanism between tubular element 9 and inner catheter 4, cushion 5 and inner catheter 4, as well as tubular sheath 7 and inner catheter 4 is advantageously provided by heat shrinking or melt sealing. It is also self-evidently possible to provide any combination of these two preferred fastening mechanisms. Polyester is regarded as a preferred material for the shrink material with selection of a connection by means of shrinking. However, in general, every thin-walled shrinking material is imaginable. In the case that a connection by means of melting is intended, polyamides, for example Nylon® or Besvoa® are regarded as preferred materials. However, as long as materials capable of melting at low temperature are producible in a thin-walled manner, they are useable in the present case.

Figure 3:
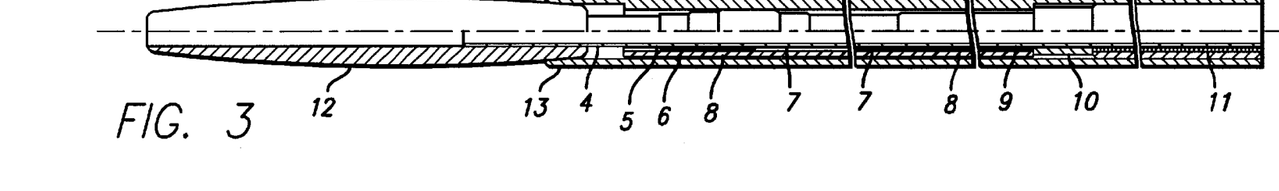
FIG. 3 shows a further embodiment of the distal end of the catheter system according to the invention.

FIG. 3 shows the same components which are also depicted in FIG. 2. However, as opposed to the embodiment of the catheter system 1 depicted in FIG. 2, the catheter system 1 of FIG. 3 is provided with a tip 12 which is adhesion bonded to the inner catheter 4.

Figure 4:
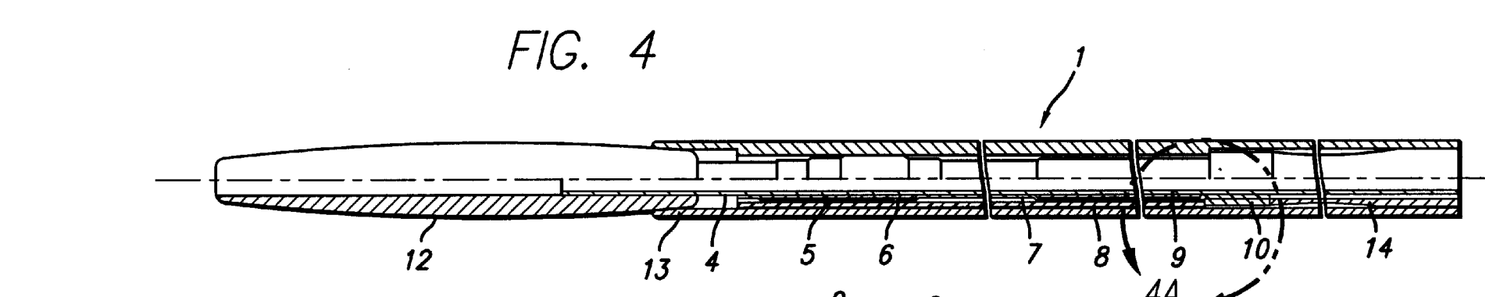
FIG. 4 shows a partially sectional side view of a further embodiment in which also the distal end region of the catheter system is depicted.
Figure 4A:
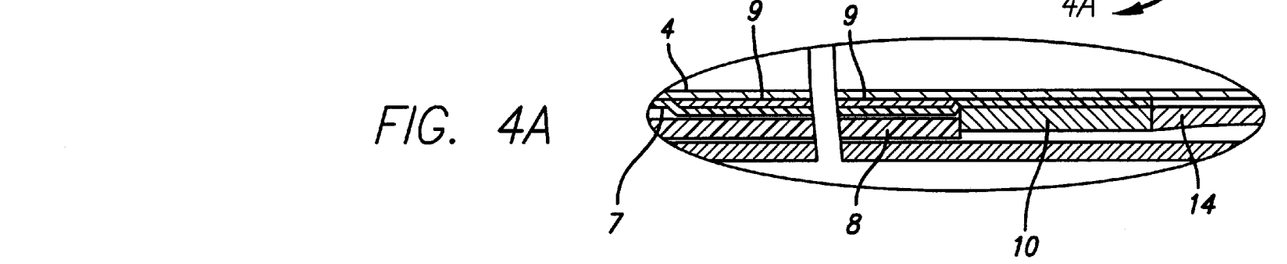

FIG. 4 illustrates a further embodiment of the catheter system 1. In this case and as opposed to the example depicted in FIG. 2, the filler material is not provided as a mechanically functioning spring element, but rather, is formed by a melt sheath 14 of plastic (Isoplast®) which is melted onto the inner catheter 4 in a melting process proximal to the proximal marker 10. For strengthening this attachment, it is also possible to encase the melt sheath 14 by an additional heat shrinkable sleeve proximal to the proximal-lying marker 10. A melt sheath 14 also prevents the proximal radiopaque marker 10 from moving in the axial direction relatively to the inner catheter 4. As with the spring 11 shown in FIG. 2 and FIG. 3, it equally forms a proximal abutment with respect to the proximal radiopaque marker 10. The selection of a melt sheath 14 also offers the advantage that this has a high flexibility despite a strong attachment to the inner catheter 4 such that deformation of the catheter system 1 up to bends in very tight radii are possible without the occurrence of mechanical failure in the form of kinks or fractures.

Figure 5:
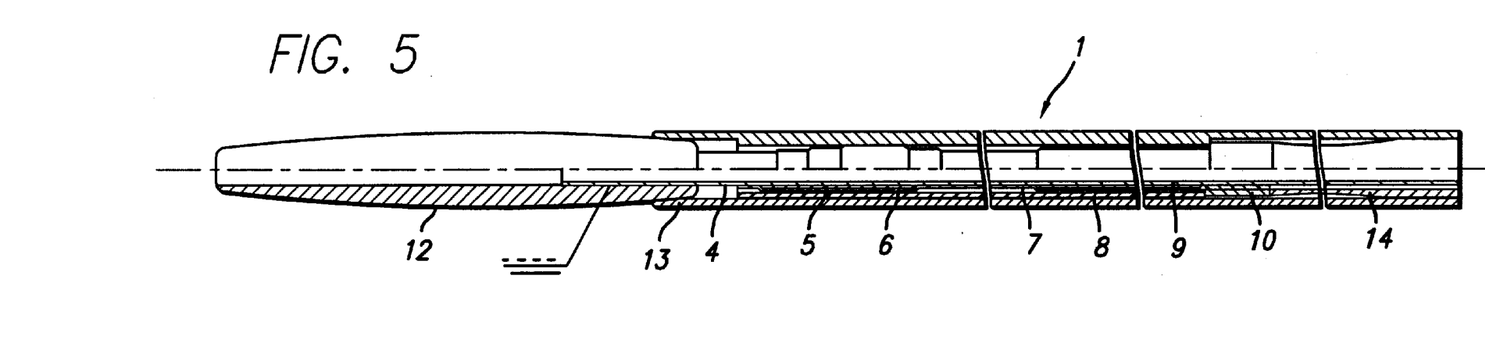
FIG. 5 shows an additional embodiment of the catheter system according to the invention, also a partially sectional side view of the distal end region of the catheter system being depicted here.

The embodiment of the catheter system 1 depicted in FIG. 5 corresponds to that depicted in FIG. 4, however, the tip 12 on the inner catheter 4 is provided with an adhesive bond. Such an adhesive bond is advantageously formed in such a manner that the flexible tip 12 consists of a transparent material and the adhesive which is used for bonding the flexible tip 12 with the inner catheter 4 is UV-curable.

Figure 6A:
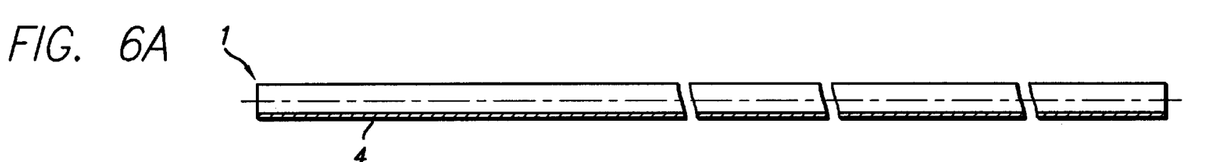
FIG. 6a to 6i illustrate the mounting process of the distal end of the catheter according to the invention in individual steps.

FIG. 6, divided into FIG. 6a to 6i, illustrates the assembly of the distal end of the catheter system 1. Thus, FIG. 6a shows the linearly formed inner catheter 4 without any steps as a starting point of the assembly process.

Figure 6B:
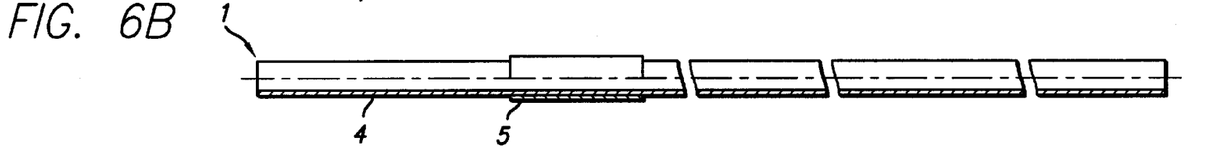

FIG. 6b shows how in a next step the cushion 5 is applied in the region of the inner catheter at which the distal radiopaque marker 6 should be found later. Thereby, cushion 5 can consist of a resilient material which is held on the catheter 4 by inherent tension, but can equally be affixed by heat shrinking or melting to the inner catheter.

Figure 6C:
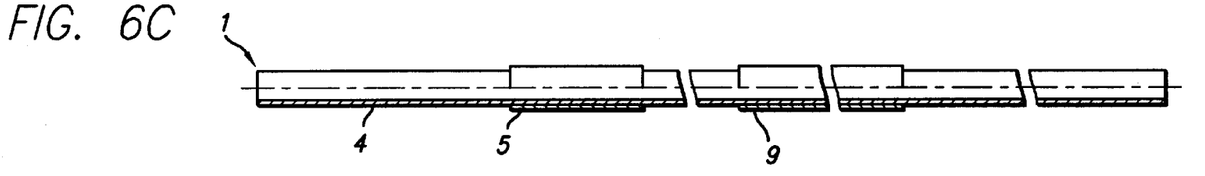

FIG. 6c illustrates how in a third mounting step the tubular element 9 is mounted either from the distal end of the catheter or from its proximal end to the inner catheter 4 and is affixed thereto. In this connection, care has to be taken that the proximal end-face of the tubular element 9 should be arranged where the distal end-face of the proximal radiopaque marker 10 is to be found.

Figure 6D:
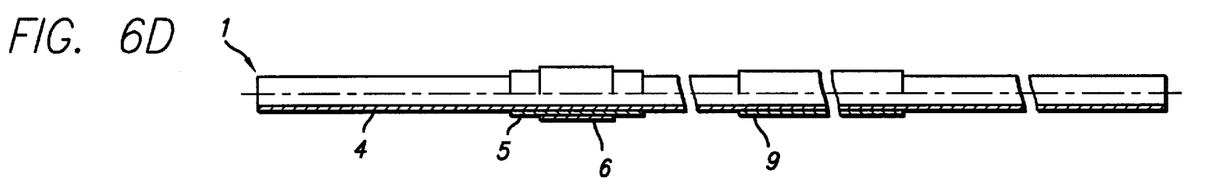

In a fourth mounting step depicted in FIG. 6d, the distal radiopaque marker 6 is applied to the middle of the cushion 5 whereby the distance between the distal radiopaque marker and proximal end-face of the tubular element 9 is selected in such a manner that it corresponds to the length of the endoprosthesis 8 to be implanted. In this manner, radial guidance of the distal end region of the endoprosthesis 8 in its mounted state is provided by the distal radiopaque marker 6.

Figure 6E:
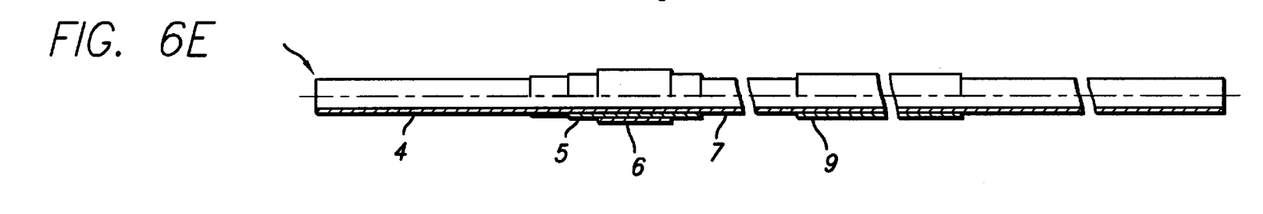

The distal radiopaque marker 6 is held in this position and in a subsequent mounting step, which is depicted in FIG. 6e, the tubular casing 7 is pulled over cushion 5, distal radiopaque marker 6 as well as tubular element 9. In a heat shrinking or melt process (not shown), the tubular casing 7 is affixed to the inner catheter 4 such that the components arranged under this are fixed axially. It is also to be noted that the tubular casing 7 protrudes over the tubular element 9 at the proximal side by an amount which is slightly broader than the width of the proximal radiopaque marker 10.

Figure 6F:
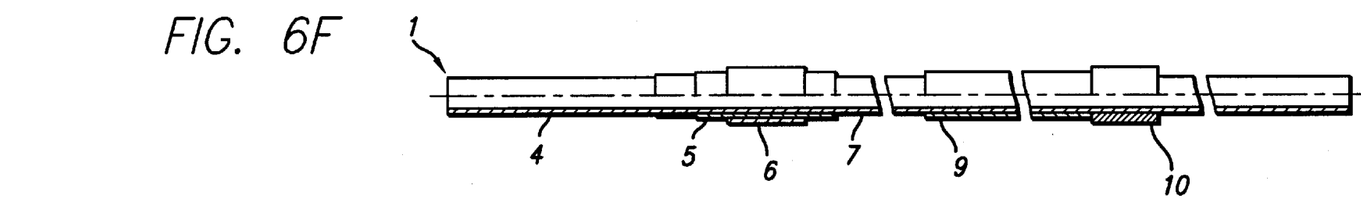

In a subsequent mounting step which is depicted in FIG. 6f, this is slid from the proximal end of the catheter system 1 onto the inner catheter 4 until the distal end-face of the proximal radiopaque marker 10 and the proximal end-face of the tubular element 9 sit on each other.

Figure 6G:
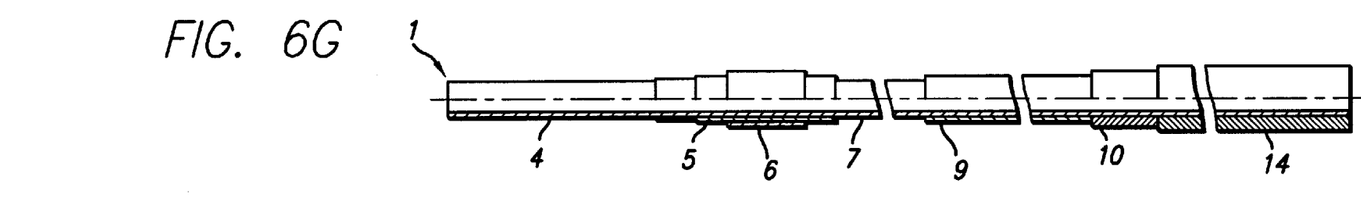

The radiopaque marker 10 is held in this position, and in a following step which is illustrated in FIG. 6g, the proximal radiopaque marker 10 is also fixed in its position.

Figure 6H:
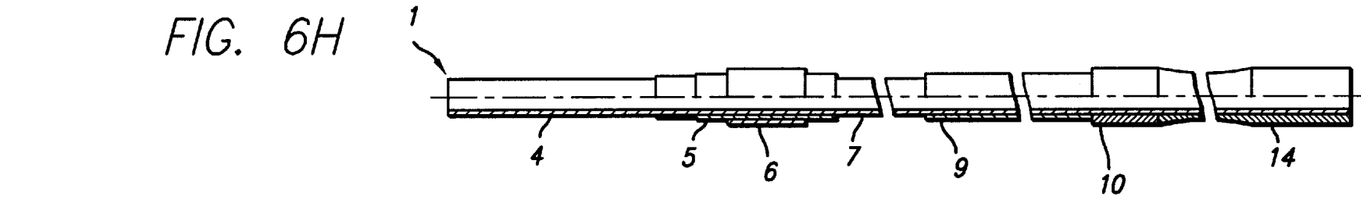

This occurs by applying the filler. This filler is attached to inner catheter 4 by heating the catheter system to the melting point of the filler material in the case that it is provided as a melt sheath 14 as depicted in FIG. 6. In the case that the filler material is formed by a mechanical spring, the form-locking effect or combined form-/forcelocking effect is provided by having the spring 11 supported distally on the proximal radiopaque marker 10 and proximally on the handle 2 not depicted in FIG. 6. The fixed state of the filler is depicted in FIG. 6h.

Figure 6I:
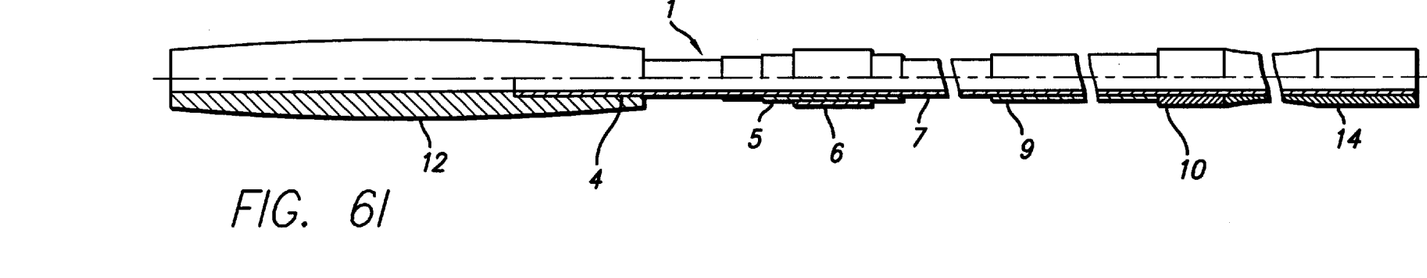

Finally, as shown in FIG. 6i, the flexible end 12 is fastened to the distal end of the inner catheter 4 by means of adhesion, heat sealing, soldering, melting or the like.

As emerges from the illustration of FIG. 6i, there is a distance between the distal end-face of the proximal radiopaque marker and the proximal end-face of the flexible tip 12. This distance corresponds to the maximal length of the endoprostheses 8 to be introduced. Such an endoprosthesis can easily be introduced in its expanded state from the distal end of the catheter system 1 over the tip 12 on the inner catheter 4 until the proximal end-face of the endoprosthesis 8 is found in the region of the abutment edge formed by the proximal radiopaque marker 10. In the following, the endoprosthesis is compressed and the outer sheath 13, which preferably consists of Isoplast®, a Nylon®-polyurethane mixture, Nylon®, Teflon® or other suitable thin-walled heat shrinkable sleeve material, is slipped from the proximal end of the catheter system 1 over the filler, the proximal radiopaque marker 10, the compressed endoprosthesis 8 and the proximal end region of the tip 12. The compressed endoprosthesis contacts the outer sheath and the condition depicted in FIGS. 2 to 5 results.

For introducing the endoprostheses 8 into a human body for example through a blood vessel, the catheter system 1 is inserted into the blood vessel until it can be recognized based on the two radiopaque markers 6, 10 that the endoprosthesis 8 is found in the target region, i.e. the intended placement site. After that, the outer sheath 13 is pulled proximally by means of the handle 2. When the outer sheath no longer overlaps the endoprosthesis 8, the latter expands to its initial state depicted in FIG. 1 by resilient restoring force or by adopting body temperature. The catheter system can then be pulled out of the vessel substantially free of force.

It will be noted that the radiopaque markers lock the endoprosthesis into place without the use of any adhesive for fixing the rigid radiopaque markers on the catheter assembly. Hence, the problems of the prior art are avoided.

What is claimed is:

1. An endoprosthesis delivery catheter system, comprising:
    a shaft assembly extending between a proximal end portion and a distal end portion, the distal end portion being capable of carrying an endoprosthesis to a placement site;
    a ring component;
    a tubular element having a first end, in end to end facing relationship with the ring component while carried on the distal end of the shaft, and a second end remote from the first end, and
    a tubular casing being in tension around the circumference of the shaft to enhance its frictional contact with the shaft and extending along the shaft over a radially outer surface of the tubular element, and along the shaft radially inside the ring component, enabling the tubular element to resist unwanted axial sliding movement of the ring component on the shaft.

2. Catheter system according to claim 1, wherein the end-faces of the ring component and the tubular element are formed substantially perpendicular to the longitudinal extent of the shaft.

3. Catheter system according to claim 1, wherein the tubular casing is tightly fitted on the shaft by melting.

4. Catheter system according to claim 1, wherein the tubular casing is tightly fitted on the shaft by shrinking.

5. Catheter system according to claim 1, additionally comprising a further ring component within the casing, and a tubular cushion between the further ring component and the shaft.

6. Catheter system according to claim 1, wherein the tubular casing serves as a cushion to the ring component.

7. Catheter system according to claim 1, further comprising an endoprosthesis and an outer sheath, wherein the outer sheath is arranged coaxially around the tubular casing and the endoprosthesis.

8. Catheter system according to claim 7, wherein the endoprosthesis is a self-expanding prosthesis.

9. Catheter system according to claim 8, wherein the endoprosthesis has resilient restoring forces which bring about self-expansion.

10. Catheter system according to claim 9, wherein the self-expansion of the endoprostheses is triggered by temperature change.

11. Catheter system according to claim 1, wherein the ring component is a radiopaque marker.

12. Catheter system according to claim 1, additionally comprising a flexible tip which is fixed to the distal end of the shaft by an adhesive.

13. Catheter system according to claim 12, wherein the adhesive is one which is curable by ultra-violet radiation.

14. Catheter system according to claim 1, additionally comprising a flexible tip which is fixed on the distal end of the shaft by melting.

15. Catheter system according to claim 1 wherein the tubular casing is of polyamide.

16. Catheter system according to claim 1 wherein the tubular element is of polyester.

17. Catheter system according to claim 1, wherein the shaft is of polyimide or polyamide.

18. Catheter system according to claim 1 wherein the tubular element has a wall thickness in a range of from 0.03 mm to 0.1 mm.

19. Catheter system according to claim 1 wherein the tubular casing has a wall thickness in a range of from 0.03 mm to 0.1 mm.

20. Catheter system according to claim 1 wherein the inner shaft has a wall thickness of approximately 0.15 mm and an inner diameter of approximately 1.2 mm.

21. Catheter system according to claim 7 or, wherein the outer sheath has a wall thickness of approximately 0.15 mm and an inner diameter of approximately 1.8 mm.

22. Catheter system according to claim 1, as part of a delivery kit for an endoprosthesis.

23. Catheter system according to claim 8, wherein the outer sheath has a wall thickness of approximately 0.15 mm and an inner diameter of approximately 1.8 mm.

* * * * *